United States Patent [19]

Schleifstein et al.

[11] Patent Number: 4,954,551
[45] Date of Patent: Sep. 4, 1990

[54] HALOGEN-CONTAINING ORGANOMETALLIC COMPOUNDS

[75] Inventors: Robert A. Schleifstein, Baton Rouge, La.; Mohammed A. Khuddus, Matawan, N.J.

[73] Assignee: Ethyl Corporation, Richmond, Va.

[21] Appl. No.: 331,163

[22] Filed: Mar. 31, 1989

[51] Int. Cl.$^5$ .......................... C08K 5/59; C07F 9/94; C07F 9/92
[52] U.S. Cl. ...................... 524/327; 556/80
[58] Field of Search ............... 524/327, 368, 382, 412; 556/76, 80

[56] References Cited

U.S. PATENT DOCUMENTS

| | | | |
|---|---|---|---|
| 2,511,013 | 6/1950 | Rust et al. | 556/76 |
| 2,993,924 | 7/1961 | Marks et al. | 556/76 |
| 3,031,425 | 4/1962 | Schoepfle et al. | 556/80 |
| 3,359,218 | 12/1967 | Wiles | 556/76 |
| 3,407,153 | 10/1968 | Bowman et al. | 556/76 |
| 3,688,001 | 8/1972 | Exner et al. | 524/281 |
| 3,803,193 | 4/1974 | Ventura et al. | 260/446 |
| 3,833,630 | 9/1974 | Loeffler | 260/446 |
| 3,931,260 | 1/1976 | Foley et al. | 556/80 |
| 3,932,541 | 1/1976 | Davis et al. | 560/264 |
| 4,130,552 | 12/1978 | Muntz | 528/285 |
| 4,240,956 | 12/1980 | Weil et al. | 556/76 |
| 4,567,242 | 1/1986 | Nishibori et al. | 524/327 |
| 4,798,857 | 1/1989 | Bertelli et al. | 556/35 |

FOREIGN PATENT DOCUMENTS 3128875 2/1983 Fed. Rep. of Germany .
46-6865 2/1971 Japan .

OTHER PUBLICATIONS

Jha et al., "Flame Retardation of Polypropylene: Effect of Organoantimony Compounds on the Flammability and Thermal Behavior," J. of App. Poly. Science, vol. 32, pp. 4393–4403 (1986).

Primary Examiner—Veronica P. Hoke
Attorney, Agent, or Firm—E. E. Spielman, Jr.; David A. LaRose

[57] ABSTRACT

This invention relates to a compound of the formula,

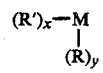

wherein: M is Sb(III) or Bi(III), x and y are whole integers and x=1, 2 or 3, y=0, 1 or 2 and x+y=3; each R is independently selected from hydroxy radicals, alkoxy radicals and phenoxy radicals; and each R' is independently selected from haloalkoxy radicals and halophenoxy radicals in which each halo constituent is independently selected from bromine or chlorine. Such compounds are useful flame retardants.

6 Claims, No Drawings

HALOGEN-CONTAINING ORGANOMETALLIC COMPOUNDS

BACKGROUND OF THE INVENTION

This invention relates to novel halogen-containing organometallic compounds and their use as flame retardants.

Flammable macromolecular materials, e.g. thermoplastic formulations, can be rendered flame retardant by treatment with a combination of antimony or bismuth trioxide and a halogen-containing compound. The trioxides act as synergists and enable a reduction in the amount of halogen-containing compound needed to obtain the desired flame retardant effect. It is not fully understood how these trioxides operate to allow for this reduction, however, it is postulated that the antimony or bismuth trioxide react with the halogen provided by the halogen-containing compound to form antimony or bismuth trihalides or oxyhalides. A decomposition mechanism has been proposed in which these trihalides or oxyhalides decompose in a stepwise manner and thus participate directly in flame-quenching reactions.

Application or incorporation of the antimony or bismuth trioxide and the halogen-containing compound onto or into the macromolecular material is generally accomplished by coating, blending or mixing. Due to the fine particle size and toxicity of the trioxides, care must be taken during these procedures so as to not contaminate the workplace.

While industry has developed techniques to insure safe handling of these trioxides, these techniques add cost to the flame retarding of the macromolecular material. To avoid these costs, it would be desirable to have a flame retardant system which does not require the use of antimony or bismuth trioxide but which still maintains the presence of antimony or bismuth in the flame retardant system and thereby enjoys the benefits thereof.

To this end, therefore, it is an object of this invention to provide novel halogen-containing organometallic compounds which exhibit excellent flame retardancy without the presence of antimony or bismuth trioxide. It is also an object of this invention to provide novel halogen-containing organometallic compounds which have other uses, such as, polycondensation catalysts.

THE INVENTION

This invention relates to antimony (III) or bismuth (III) derivatives of haloalcohols and halophenols. Exemplary of such derivatives are antimony (III) haloalkoxides, antimony (III) halophenoxides, antimony (III) haloalkoxide-halophenoxides, bismuth (III) haloalkoxides, bismuth (III) halophenoxides and bismuth (III) haloalkoxide-halophenoxides and oligomers thereof. These compounds, individually and in mixture, are useful flame retardants and can be represented by the formula,

in which M is Sb (III) or Bi(III), x and y are whole integers, $x=1$, 2 or 3, $y=0$, 1 or 2 and $x+y=3$; each R is independently selected from hydroxy, alkoxy and phenoxy radicals and each R' is independently selected from haloalkoxy and halophenoxy radicals, in which each halo constituent is independently selected from chlorine or bromine.

Since hydroxy radicals do not contribute significantly to the fuel value of the compound, it is preferred that R be such a radical. Should R be an alkoxy or a phenoxy radical, it is advisable, from a fuel value standpoint, to keep the number of carbon constituents in R as small as is practical. Suitable alkoxy radicals or butoxy, ethoxy, isopropoxy, pentoxy, neopentoxy radicals and the like. Exemplary of suitable phenoxy radicals are phenoxy, 4,4'-isopropylidene diphenoxy, resorcinoxy, 4,4'-methylene diphenoxy radicals and the like.

The R' haloalkoxide and halophenoxide radicals are obtained from precursor haloalcohols and halophenols. Suitable haloalkoxides include monohalodihydroxyneopentoxide, dihalohydroxyneopentoxide, trihaloneopentoxide, dibromopropoxide, bromoethoxide, and 2,3-dibromobuteneoxy. A preferred compound of this invention is one in which each R' is dihalohydroxyneopentoxide. The bromo species of this haloalkoxide is derived from the commercially available bromoalcohol, dibromoneopentyl glycol. Another family of preferred compounds of this invention are those in which each R' is independently selected from monohalodihydroxyneopentoxide, dihalohydroxyneopentoxide and trihaloneopentoxide. The mix of bromoalcohols from which R' can be derived in this case is commercially available and conveniently prepared in accordance with U.S. Pat. No. 3,932,541.

It is preferred, when R' is a halophenoxy radical, that the halophenoxy radical be chosen from,

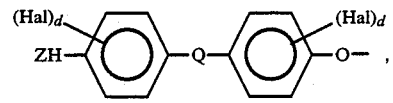

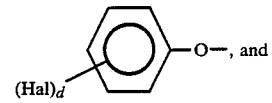

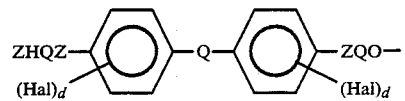

wherein Q is a sulfone or an alkylene or an alkylidene radical containing up to 4 carbon atoms, each Z is independently —O— or —S—, each Hal is independently chlorine or bromine, and each d is independently 1, 2, 3, or 4. Preferred of these are,

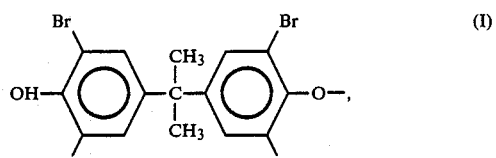

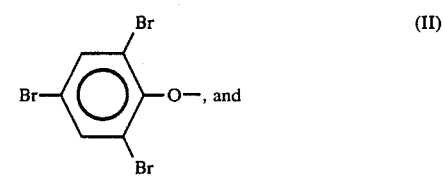

-continued

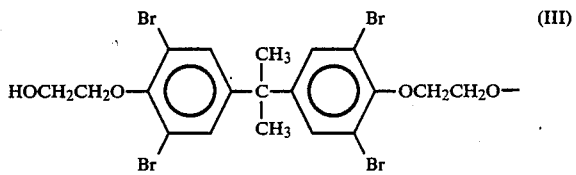

The bromophenols from which the foregoing are derived are wellknown. (I) is derived from tetrabromobisphenol-A, (II) from 2,4,6-tribromophenol, and (III) from tetrabromobisphenol-A-bis(2-hydroxyethyl ether). The most preferred halophenoxide is (I). Though not necessarily preferred, halophenoxides which are derived from halophenols, such as pentabromophenol, tetrabromobisphenol-S, 4,4'-dihydroxy-2,2',3,3',5,5',6,6'-octabromidiphenyl oxide, tetrabromobisphenol-F, tetrabromobisphenol E, tetrabromoresorcinol, tetrabromobisphenol-AF, tetrachlorophenol, dibromodichlorophenol, tetrachlorobisphenol A, and the like, are suitable.

When the haloalkoxy or halophenoxy radical is derived from a haloalkanol or halophenol having two or more hydroxy functional groups, as would be the case for dibromoneopentyl glycol and for I and III, it is probable that there will be some antimony or bismuth bonding at both hydroxy sites. The resultant compound will then be oligomeric in nature. In this case, the product from the process used to produce the compound of this invention will contain both monomeric and oligomeric species. The oligomeric species function as flame retardants and their presence in the product is not known to be detrimental.

Since, in most flame retardant applications, bromine is more efficacious than chlorine, the preferred halo constituent is bromine.

Due to the wide acceptance by industry of the use of antimony trioxide as a synergist with many halogen-containing flame retardants, M is preferably Sb(III).

When the compounds of this invention are used as flame retardants, it is desirable that the atomic ratio of the halo constituent to the M radical in the compound be substantially the same as that provided by the conventional combination of halogen-containing flame retardants and antimony or bismuth trioxides. Thus, for the compounds of this invention, it is preferred that there be no more than 7 halo constituents in the molecule per M constituent. This is not to say that more halo constituents cannot be present, but rather only that the synergism provided by the halo constituents and the M radical will be lost to those halo constituents for which there are no M radicals available. Obtainment of the desired atomic ratio can be achieved by selecting the proper combination of R' and value for x.

The amount of the compound of this invention which is necessary to provide the desired degree of flame retardancy will be dependent upon the particular flammable macromolecular material being treated, the manner of treatment, e.g. coating, mixing, etc., the presence of other additives and the shape of the final article produced from the macromolecular material. In most instances, the determination of the correct amount will be made by trial and error with the goal being to use the least amount of compound needed to achieve the desired degree of flame retardancy. As a general guide, when the macromolecular material is a thermoplastic or thermoset material, the parts by weight of compound used will be within the range of from about 1 to about 40 per 100 parts of total formulation.

Exemplary of several of the thermoplastic or thermoset materials which are suitable for use with the compound of this invention are polyolefins, ethylene/ethyl acrylate copolymers and ethylene/vinyl acetate copolymers; polymers of olefinically unsaturated monomers, for example, polystyrenes, e.g. high impact polystyrene and styrene copolymers; polyurethanes; polyamides; polyimides; polycarbonates; polyethers; acrylic resins; polyesters, especially poly(methyleneterephthalate), poly(ethyleneterephthalate) and poly(butyleneterephthalate); epoxy resins; alkyds; phenolics; elastomers, for example, butadiene/styrene copolymers and butadiene/acrylonitrile copolymers; terpolymers of acrylonitrile, butadiene and styrene; natural rubber; butyl rubber; and polysiloxanes. The polymer may also be a blend of various polymers. The composition may contain any of the additives usually present and where appropriate to the particular polymers, may be crosslinked by chemical means or by irradiation.

The compounds of this invention can be produced by the reaction of the haloalcohol or halophenol precursor of R' with antimony (III) or bismuth (III) alkoxide or phenoxide. If the production of oligomeric species is of concern, the antimony (III) or bismuth (III) reactants should be added slowly to a well stirred solution of the haloalcohol or halophenol precursor to thereby minimize this production.

Should the reaction form the compound of this invention in which R is an alkoxide or a phenoxide radical and it is desired instead that R be a hydroxide radical, the compound can be subjected to a hydrolysis reaction to effect the conversion of the alkoxide or phenoxide radical to a hydroxide radical. For example, a useful hydrolysis technique would be to expose the compound to an aqueous acid or alkali solution followed by the removal of the liberated alcohol or phenol.

Examples I–III illustrate the above method of producing compounds of this invention.

EXAMPLE I

A three-liter, four-necked flask equipped with a thermometer, mechanical stirrer, condenser, nitrogen inlet and an addition funnel was heated to 100° C and cooled to room temperature. The flask was then purged with nitrogen. To this flask was charged a homogenous solution of tetrabromobisphenol-A in butanol (326 g of tetrabromobisphenol-A [0.6 moles] in 1200 cc of butanol). After charging, the solution was agitated. Then, over a period of 10 minutes, 136 g of tris antimony butoxide (0.4 moles) was slowly charged to the flask. Vigorous agitation was provided during the charging. A precipitated product was then recovered by filtration. The product was washed with 50 cc of butanol and sucked to dryness. The partially dried product was then dried overnight in a forced air oven at 120° C. to give a dry product in 70% yield (262 g) with a Br content of 48% and a Sb content of 15.7%.

The production of a compound of this invention by the foregoing process can be illustrated by the following,

-continued

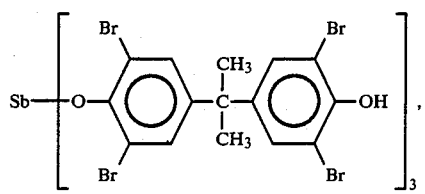

TBBPA is tetrabromobisphenol-A.

TBBPA is tetrabromobisphenol-A.

EXAMPLE II

A 500 cc, four-necked flask equipped with a thermometer, mechanical stirrer, condenser, nitrogen inlet and an addition funnel was heated to 100° C., cooled to room temperature and then purged with nitrogen. To the flask was charged a homogeneous solution of dibromoneopentyl glycol (39.3 g of dibromoneopentyl glycol [0.15 moles] in 300 cc of butanol). The solution was agitated. Then, 34.1 g of tris-antimony butoxide (0.1 mole) was added slowly to the flask over a period of 10 minutes with vigorous agitation of the reaction mass. 250 cc of butanol was distilled off at 120° C. The reaction mass was then cooled to room temperature. A precipitate was recovered by filtration and washed with 20 cc of butanol and sucked to dryness. The partially dried precipitate was further dried in a forced hot air oven at 120° C. to give 39 g of dry precipitate (76% weight yield) with a melting point of 244°-246° C. and a Br content of 41.3% and Sb content of 24.2%.

The production of a compound of this invention by the foregoing process reaction can be represented by

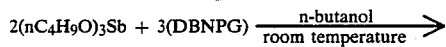

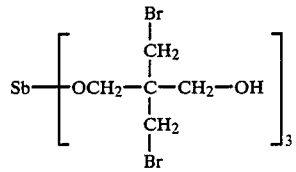

DBNPG is dibromoneopentyl glycol.

DBNPG is dibromoneopentyl glycol.

EXAMPLE III

A 500 cc, four-necked flask equipped with a thermometer, mechanical stirrer, condenser, nitrogen inlet and an addition funnel was heated to 100° C., cooled to room temperature and purged with nitrogen. To this flask was charged a butanol solution of a mixture of dibromoneopentyl glycol and tetrabromobisphenol-A. The resultant solution contained 19.7 g of dibromoneopentyl glycol (0.75 mole) and 40.8 g of tetrabromobisphenol-A (0.75 mole) and 300 cc of butanol. To this solution was slowly added 34.1 g of tris antimony butoxide (0.1 mole) over a period of 10 minutes with vigorous agitation. After the addition was complete, 250 cc of butanol was distilled off at 120° C. The distilland was then cooled to room temperature. A solid product was recovered by filtration and then washed with 20 cc of butanol and sucked to dryness. The partially dried product was dried overnight in a forced hot air oven at 120° C. to give 63 g of dry product (85% weight yield) with a Br content of 48.4% and a Sb content of 16.4%.

The products obtained can be of the Example I type, the Example II type, or of the type in which each R' is independently selected from dibromohydroxyneopentoxide and the halophenoxide derived from tetrabromobisphenol-A.

It has been found that the yields and the Sb content of the reaction products can be raised if the above reactions are carried out at higher temperatures.

The $(nC_4H_9O)_3Sb$ reactant can be prepared by the route,

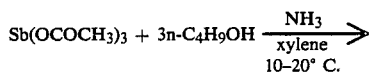

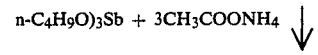

See U.S. Pat. No. 3,830,193.

Plaques were prepared from the formulations shown in Tables I and II. The formulations were prepared in Table I by mixing the ingredients in a Banbury mixer at 175° C. to provide a substantially homogeneous mix. The resultant mix was formed into pellets. The formulation in Table II was prepared by forming a substantially homogeneous mix with a twin screw extruder at 250° C. The resultant strand from the extruder was chopped to form pellets. The plaques in Table I were prepared by injection molding of the pellets at 200°-230° C. The plaque in Table II was prepared by injection molding of the pellet at 260° C.

TABLE I

| | Plaque No. 1 | Plaque No. 2 |
| --- | --- | --- |
| Cycolac T-1000 | 43.2 g | 35 g |
| Tetrabromobisphenol-A (58.4% Br) | 14.4 g | — |
| Compound A (46.7% Br; 13.3% Sb) | — | 15 g |
| $Sb_2O_3$ | 2.4 g | — |
| UL-94 (⅛") (1/16") | V-O | V-O |
| U.V. Stability (48 hours) | | |
| Y.I. (initial) (ASTM 313) | 25.83 | 27.59 |
| Y.I. (final) (ASTM 313) | 60.39 | 52.71 |
| $\Delta E_{48}$ | 22.23 | 13.28 |
| % Br in formulation | 14.0 | 14.0 |
| % Sb in formulation | 3.3 | 4.0 |

Cycolac T-1000 is an ABS resin sold by Borg Warner.
Compound A was prepared by the procedure of Example I and contains the indicated percentages of Br and Sb(III).
$\Delta E_{48}$ is the total color difference after 48 hours of exposure in a Sunlighter 150 test cabinet as measured by a Hunter Associates Laboratory Inc. Lab Scan ® II.

TABLE II

| PBT Valox ® 420 | 960 g |
| --- | --- |
| Compound B (47.9% Br/15.7% Sb) | 240 g |
| UL-94 (⅛") (1/16") | V-O |
| U.V. Stability | |
| Y.I. (initial) (ASTM 313) | 12.30 |
| Y.I. (final) (ASTM 313) | 37.95 |
| $E_{48}$ | 12.08 |
| H.D.T. ¼" °C. (ASTM D-648) | 185 |
| Melt Flow 2/10 min. (ASTM D-1238) | 10.8 |
| Izod ft lb/in (ASTM D-256) | 1.0 |
| O.I. (ASTM 2863) | 41.9 |
| % Br in formulation | 9.6 |

TABLE II-continued

| % Sb in formulation | 3.1 |

PBT Valox ® 420 polybutyleneterephthalate resin is available from General Electric Company.

Compound B was prepared by the procedure of Example I and contains the indicated percentages of Br and Sb(III).

What is claimed:

1. A compound of the formula

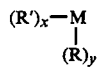

wherein: M is Sb(III) or Bi(III), x and y are whole integers and x=1, 2, or 3, y=0, 1 or 2 and x+y=3; each R is independently selected from hydroxy radicals, alkoxy radicals and phenoxy radicals; and each R' is

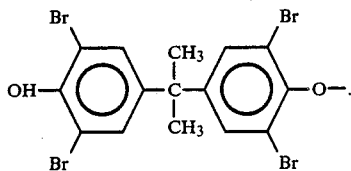

2. The compound of claim 1 wherein M is Sb(III).
3. The compound of claim 2 wherein x equals 3.
4. A formulation comprising a flammable macromolecular material and a flame retardant amount of the compound of claim 1.
5. A formulation comprising a flammable macromolecular material and a flame retardant amount of the compound of claim 2.
6. A formulation comprising a flammable macromolecular material and a flame retardant amount of the compound of claim 3.

* * * * *

UNITED STATES PATENT AND TRADEMARK OFFICE
CERTIFICATE OF CORRECTION

PATENT NO. : 4,954,551

DATED : SEPTEMBER 4, 1990

INVENTOR(S) : ROBERT A. SCHLEIFSTEIN, ET AL.

It is certified that error appears in the above-identified patent and that said Letters Patent is hereby corrected as shown below:

Title page, Attorney's name, reads "David A. LaRose", and should read -- David E. LaRose --.

Signed and Sealed this

Thirty-first Day of December, 1991

Attest:

HARRY F. MANBECK, JR.

*Attesting Officer*  *Commissioner of Patents and Trademarks*